(12) United States Patent
Shan et al.

(10) Patent No.: US 7,550,405 B2
(45) Date of Patent: *Jun. 23, 2009

(54) ZEOLITE COMPOSITE, METHOD FOR MAKING AND CATALYTIC APPLICATION THEREOF

(75) Inventors: Zhiping Shan, Bloomfield, NJ (US); Peter Wilhelm Gerhard Waller, Delft (NL); Bowden George Maingay, The Hague (NL); Philip J. Angevine, Woodbury, NJ (US); Jacobus Cornelis Jansen, Delft (NL); Chuen Y. Yeh, Edison, NJ (US); Thomas Maschmeyer, Delft (NL); Frits M. Dautzenberg, Mahwah, NJ (US); Leonardo Marchese, Grugliasco (IT); Heloise de Oliveira Pastore, Campinas (BR)

(73) Assignee: Lummus Technology Inc., Bloomfield, NJ (US)

( * ) Notice: Subject to any disclaimer, the term of this patent is extended or adjusted under 35 U.S.C. 154(b) by 167 days.

This patent is subject to a terminal disclaimer.

(21) Appl. No.: 11/446,320

(22) Filed: Jun. 2, 2006

(65) Prior Publication Data
US 2006/0264318 A1    Nov. 23, 2006

Related U.S. Application Data

(63) Continuation of application No. 10/691,358, filed on Oct. 22, 2003, now Pat. No. 7,084,087, which is a continuation-in-part of application No. 09/995,227, filed on Nov. 27, 2001, now Pat. No. 6,762,143, which is a continuation-in-part of application No. 09/390,276, filed on Sep. 7, 1999, now Pat. No. 6,358,486.

(51) Int. Cl.
*B01J 29/06* (2006.01)
(52) U.S. Cl. .................. 502/64; 502/63; 502/66; 502/71; 502/74; 502/77; 502/78; 502/79
(58) Field of Classification Search .................. 502/63, 502/64, 66, 71, 74, 77, 78, 79
See application file for complete search history.

(56) References Cited

U.S. PATENT DOCUMENTS

| 5,057,296 A | 10/1991 | Beck |
| 5,098,684 A | 3/1992 | Kresge et al. |
| 5,108,725 A | 4/1992 | Beck et al. |
| 5,110,572 A | 5/1992 | Calabro et al. |
| 5,191,134 A | 3/1993 | Le |
| 5,191,148 A | 3/1993 | Degnan et al. |
| 5,221,648 A | 6/1993 | Wachter |
| 5,264,203 A | 11/1993 | Beck et al. |
| 5,601,798 A | 2/1997 | Cooper et al. |
| 5,800,800 A | 9/1998 | Pinnavaia et al. |
| 5,811,612 A | 9/1998 | Girotti et al. |
| 5,849,258 A | 12/1998 | Lujano et al. |
| 6,133,186 A | 10/2000 | Gosselink et al. |
| 6,346,140 B2 | 2/2002 | Miyazawa et al. |
| 6,558,647 B2 | 5/2003 | Lacombe et al. |
| 6,762,143 B2 | 7/2004 | Shan et al. |
| 6,814,950 B1 | 11/2004 | Shan et al. |
| 7,084,087 B2 * | 8/2006 | Shan et al. ............. 502/64 |
| 2002/0131930 A1 | 9/2002 | Pinnavaia et al. |

FOREIGN PATENT DOCUMENTS

| EP | 0847802 | 6/1998 |
| WO | WO 97/20016 | 6/1997 |
| WO | WO 01/17901 | 3/2001 |
| WO | WO 01/21562 | 3/2001 |
| WO | WO 03/045548 | 6/2003 |

* cited by examiner

*Primary Examiner*—Elizabeth D Wood
(74) *Attorney, Agent, or Firm*—Dilworth & Barrese, LLP

(57) ABSTRACT

A catalytic material includes microporous zeolites supported on a mesoporous inorganic oxide support. The microporous zeolite can include zeolite Beta, zeolite Y (including "ultra stable Y"—USY), mordenite, Zeolite L, ZSM-5, ZSM-11, ZSM-12, ZSM-20, Theta-1, ZSM-23, ZSM-34, ZSM-35, ZSM-48, SSZ-32, PSH-3, MCM-22, MCM-49, MCM-56, ITQ-1, ITQ-2, ITQ-4, ITQ-21, SAPO-5, SAPO-11, SAPO-37, Breck-6, ALPO$_4$-5, etc. The mesoporous inorganic oxide can be e.g., silica or silicate. The catalytic material can be further modified by introducing some metals e.g. aluminum, titanium, molybdenum, nickel, cobalt, iron, tungsten, palladium and platinum. It can be used as catalysts for acylation, alkylation, dimerization, oligomerization, polymerization, hydrogenation, dehydrogenation, aromatization, isomerization, hydrotreating, catalytic cracking and hydrocracking reactions.

23 Claims, 12 Drawing Sheets

US 7,550,405 B2

ZEOLITE COMPOSITE, METHOD FOR MAKING AND CATALYTIC APPLICATION THEREOF

CROSS-REFERENCE TO RELATED APPLICATIONS

The present application is a continuation of U.S. patent application Ser. No. 10/691,358 filed Oct. 22, 2003 and now issued as U.S. Pat. No. 7,084,087, which is a continuation-in-part of U.S. patent application No. 09/995,227, filed on Nov. 27, 2001 and now issued as U.S. Pat. No. 6,762,143, which is a continuation in part of U.S. patent application No. 09/390,276 filed Sep. 7, 1999, and now issued as U.S. Pat. No. 6,358,486, to which priority is claimed, both of said applications being herein incorporated by reference.

BACKGROUND

1. Field of the Invention

The present disclosure is related to a unique, catalytic material containing zeolite embedded in a catalyst support, and particularly to a microporous zeolite embedded in a mesoporous support.

2. Background of the Art

Many of today's hydrocarbon processing technologies are based on zeolite catalysts. Zeolite catalysts are well known in the art and possess well-arranged pore systems with uniform pore sizes. However, these materials tend to possess either only micropores or only mesopores, in most cases only micropores. Micropores are defined as pores having a diameter of less than about 2 nm. Mesopores are defined as pores having a diameter ranging from about 2 nm to about 50 nm. The small micropores limit external molecules to access the catalytic active sites inside of the micropores or slow down the diffusion process to the catalytic active sites. Many catalytic reactions of hydrocarbons are mass-transfer limited, so the effective utilization of the catalyst is reduced. One solution is to reduce the catalyst particle size, thereby shortening the diffusion path and increasing the external surface of the catalyst particles.

In practice, the small zeolite catalyst particles cannot be directly used because the dust-like material is difficult to handle, and it would create a pressure drop problem in a fixed bed reactor. As such, the zeolites are usually mixed with an inorganic oxide and extruded into a certain shape and size. The calcined, finished catalyst then has good physical integrity and a porous structure. However, depending upon the specific reaction, the binder can impose a mass-transfer limitation to the zeolite particles buried inside the binder. If the less porous binder can be replaced by a highly porous support, the accessibility of external molecules to active sites in zeolites will be increased.

It is highly desired to have a catalyst with ideal pore size distribution, which will facilitate transport of the reactants to active catalyst sites and transport of the products out of the catalyst.

SUMMARY OF THE INVENTION

A material useful in catalytic processing of hydrocarbons is provided herein. The material comprises a zeolite, and a porous inorganic oxide that includes at least 97 volume percent mesopores based on the micropores and mesopores of the inorganic oxide. The zeolite is preferably a microporous zeolite such as for example, zeolite Beta, zeolite Y (including "ultra stable Y"—USY), mordenite, Zeolite L, ZSM-5, ZSM-11, ZSM-12, ZSM-20, Theta-1, ZSM-23, ZSM-34, ZSM-35, ZSM-48, SSZ-32, PSH-3, MCM-22, MCM-49, MCM-56, ITQ-1, ITQ-2, ITQ-4, ITQ-21, SAPO-5, SAPO-11, SAPO-37, Breck-6, ALPO$_4$-5, etc. A method for making and method for using the material are described herein. The zeolite particles are surrounded by randomly interconnected mesoporous channels, which provide high accessibility to the zeolite. In some cases the interaction between the zeolite particle and mesoporous support may modify the properties of both zeolite and mesoporous support to certain extent.

The catalytic material described herein advantageously facilitates the transport of reactants to active catalyst sites and is about 2-5 times more active than the zeolite used alone, depending on the specific applications.

BRIEF DESCRIPTION OF THE DRAWINGS

Several embodiments are described below with reference to the drawings wherein.

DETAILED DESCRIPTION OF PREFERRED EMBODIMENT(S)

Figure 1:
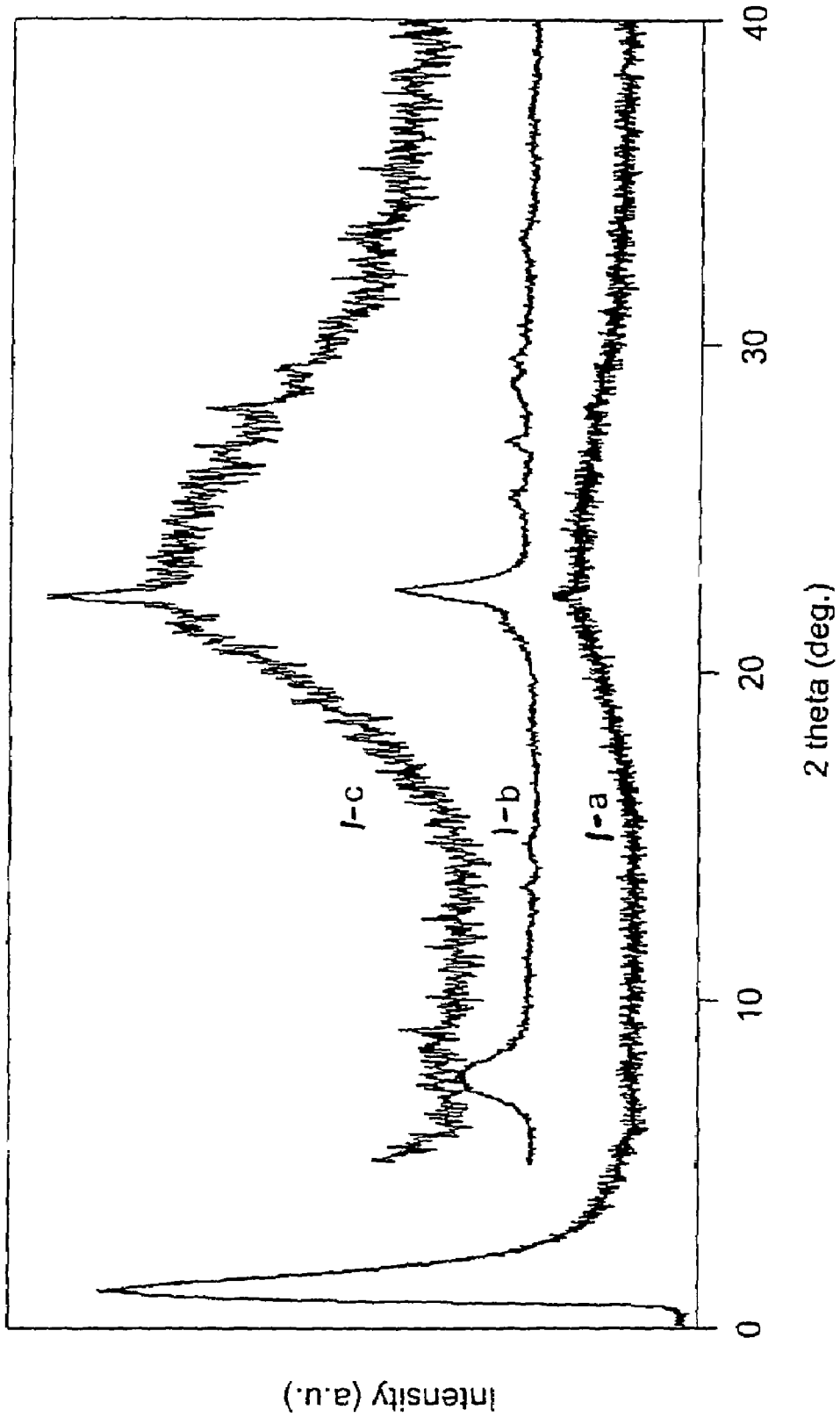
FIG. 1 shows the following: an X-ray diffraction (XRD) pattern of Sample 1 containing a mesoporous inorganic oxide support with zeolite beta (plot 1-a), an XRD pattern of zeolite beta (plot 1-b), and an extended scanning time (EST) XRD image of Sample 1 (plot 1-c)

The catalyst described herein includes a microporous zeolite embedded in a mesoporous support. The microporous zeolite can be any type of microporous zeolite. Some examples are zeolite Beta, zeolite Y (including "ultra stable Y"—USY), mordenite, Zeolite L, ZSM-5, ZSM-11, ZSM-12, ZSM-20, Theta-1, ZSM-23, ZSM-34, ZSM-35, ZSM-48, SSZ-32, PSH-3, MCM-22, MCM-49, MCM-56, ITQ-1, ITQ-2, ITQ-4, ITQ-21, SAPO-5, SAPO-11, SAPO-37, Breck-6 (also known as EMT), ALPO$_4$-5, etc. Such zeolites are known in the art, and many are commercially available. In this invention, the zeolite can be incorporated into the mesoporous support or can be synthesized in-situ in the catalyst support.

A metal can be incorporated into the zeolite framework as substitutions of lattice atoms and or located inside the micropores of the zeolite. Such metals can include, for example, aluminum, titanium, vanadium, zirconium, gallium, boron, manganese, zinc, copper, gold, lanthanum, chromium, molybdenum, nickel, cobalt, iron, tungsten, palladium and platinum. These metals can be incorporated as combinations, e.g., NiMo, NiW, PtPd, etc.

The catalyst support is preferably a three-dimensional mesoporous inorganic oxide material containing at least 97 volume percent mesopores (i.e., no more than 3 volume percent micropores) based on micropores and mesopores of the organic oxide material (i.e., without any zeolite incorporated therein), and generally at least 98 volume percent mesopores. A method for making a preferred porous silica-containing catalyst support is described in U.S. Pat. No. 6,358,486. The average mesopore size of the preferred catalyst, as determined from N$_2$-porosimetry, ranges from about 2 nm to about 25 nm.

Generally, the mesoporous inorganic oxide is prepared by heating a mixture of (1) a precursor of the inorganic oxide in water, and (2) an organic templating agent that mixes well with the oxide precursor or the oxide species generated from the precursor, and preferably forms hydrogen bonds with it. The starting material is generally an amorphous material and may be comprised of one or more inorganic oxides such as silicon oxide or aluminum oxide, with or without additional metal oxides. The silicon atoms may be replaced in part by other metal atoms. These metals include, but are not limited to, aluminum, titanium, vanadium, zirconium, gallium, boron, manganese, zinc, copper, gold, lanthanum, chromium, molybdenum, nickel, cobalt, iron, tungsten, palladium and platinum. They can be incorporated into the organic oxide inside at least one mesopore wall and/or at least one mesopore surface. The additional metals may optionally be incorporated into the material prior to initiating the process for producing a structure that contains mesopores. Also after preparation of the material, cations in the system may optionally be replaced with other ions such as those of an alkali metal (e.g., sodium, potassium, lithium, etc.).

The organic templating agent, a mesopore-forming organic compound, is preferably a glycol (a compound that includes two or more hydroxyl groups), such as glycerol, diethylene glycol, triethylene glycol, tetraethylene glycol, propylene glycol, and the like, or member(s) of the group consisting of triethanolamine, triisopropanolamine, sulfolane, tetraethylene pentamine and diethylglycol dibenzoate. Preferably, the organic templating agent has a boiling point of at least about 150° C.

The mesoporous catalyst support is a pseudo-crystalline material (i.e., no crystallinity is observed by presently available x-ray diffraction techniques). The diameter of the mesopores is preferably from about 3 nm to about 25 nm. The surface area of the catalyst support, as determined by BET (N$_2$), preferably ranges from about 400 m$^2$/g to about 1200 m$^2$g. The catalyst pore volume preferably ranges from about 0.3 cm$^3$/g to about 2.2 cm$^3$/g. According to one embodiment the materials have one peak in the XRD diffraction pattern where 2θ is between 0.5 and 2.5 degrees.

The catalyst's zeolite content can range from less than about 1% by weight to more than about 99% by weight. However, it is preferably from about 3% by weight to 90% by weight, and more preferably from about 4% by weight to about 80% by weight. The catalyst with zeolite included preferably contains no more than about 10 volume percent of micropores.

More particularly, the method for making the catalyst includes suspending a zeolite in water. An inorganic oxide precursor is then added to the water and mixed. The inorganic oxide precursor can be a silicon containing compounds such as tetraethyl orthosilicate (TEOS) or a source of aluminum such as aluminum isopropoxide, which reacts with water to form the inorganic oxide. TEOS and aluminum isopropoxide are commercially available from known suppliers.

The pH of the above mixture is preferably kept about 7.0. Optionally, the aqueous mixture can contain other metal ions such as those indicated above. After stirring, an organic templating agent is added and mixed into the mixture. The organic templating agent helps to form the mesopores during a pore-forming step, as discussed below. The organic templating agent should not be so hydrophobic so as to form a separate phase in the mixture. The organic templating agent can be one or more compounds as listed above. The organic templating agent is preferably added by dropwise addition with stirring to the aqueous inorganic oxide solution. After a period of time (e.g., from about 1 to 4 hours) the mixture forms a thick gel. The mixture is preferably stirred during this period of time to facilitate the mixing of the components. The solution preferably includes an alcohol, which can be added to the mixture and/or formed in-situ by the decomposition of the inorganic oxide precursor. For example, TEOS, upon heating, produces ethanol. Propanol may be produced by the decomposition of aluminum isopropoxide.

Optionally, the zeolite can be altered by pretreatment. For example, in one type of pretreatment the zeolite can be modified by ion exchange, impregnation, immobilization of functional species and steaming. Also, lamellar structured zeolites such as MCM-22 can be exfoliated by appropriate treatments to new types of zeolites such as ITQ-2. Certain treatments, such as intercalation or delamination, can be carried out by swelling the precursors with cationic surfactants in the presence of alkali (Corma et al. J. Catal. 191 (1): 218-224, 2000). Optionally, the swollen materials can be delaminated by, for example, ultrasonic treatment with or without mechanical agitation. Finally, the delaminated materials can be separated and calcined to form a new type of zeolite.

This invention provides a new approach to incorporate or stabilize or support the delaminated zeolite into a porous matrix/support. The swollen materials can be suspended in water first and then an inorganic oxide precursor, or the mesoporous support can be added to the water and mixed as described above. Optionally, the delamination of the swollen materials can be carried out by ultrasonic treatment with or without mechanical agitation during the addition of other components (e.g., pore-forming agent) and/or during the gel formation process. After gel formation, a new type of zeolite, differing from the zeolite added before swelling, can be incorporated into the gel.

The gel is then optionally aged at a temperature of from about 5° C. to about 45° C., preferably at room temperature, to complete the hydrolysis and polycondensation of the inorganic oxide source. Aging preferably can take place for up to about 48 hours, generally from about 0 hours to 30 hours, more preferably from about 2 hours to 20 hours. After the aging step the gel is heated in air at about 98° C. to 100° C. for a period of time sufficient to dry the gel by driving off water (e.g., from about 6 to about 48 hours). Preferably, the organic templating agent, which helps form the mesopores, should remain in the gel during the drying stage. Accordingly, the preferred organic templating agent has a boiling point of at least about 150° C.

The dried material, which still contains the organic templating agent, is heated to a temperature at which there is a substantial formation of mesopores. The pore-forming step is conducted at a temperature above the boiling point of water and up to about the boiling point of the organic templating agent. Generally, the mesopore formation is carried out at a temperature of from about 100° C. to about 250° C., preferably from about 150° C. to about 200° C. The pore-forming step can optionally be performed hydrothermally in a sealed vessel at autogenous pressure. The size of the mesopores and volume of the mesopores in the final product are influenced by the length and temperature of the hydrothermal step. Generally, increasing the temperature and duration of the treatment increases the mesopore diameter and the percentage of mesopore volume in the final product.

After the pore-forming step, the material is calcined between about 300° C. to about 1000° C. The calcination temperature is preferably from about 400° C. to about 700° C., and more preferably from about 500° C. to about 600° C. The calcining temperature is maintained for a period of time sufficient to effect removal of the organic templates/pore forming agents. The duration of the calcining step typically ranges from about 2 hours to about 40 hours, preferably 5 hours to 15 hours, depending, in part, upon the calcining temperature.

To prevent hot spots the temperature should be raised gradually. Preferably, the temperature of the catalyst material should be ramped up to the calcining temperature at a rate of from about 0.1° C./min. to about 25° C./min., more preferably from about 0.5° C./min. to about 15° C./min., and most preferably from about 1° C./min. to about 5° C./min.

During calcinion the structure of the catalyst material is finally formed while the organic molecules are expelled from the material and decomposed.

The calcinating process to remove organic templating agent can be replaced by extraction using organic solvents, e.g., ethanol. In this case the templating agent can be recovered for re-use.

Also, the catalyst powder of the present invention can be admixed with binders such as silica and/or alumina, and then formed into desired shapes (e.g., extrudates, pellets, rings, etc.) by extrusion or other suitable methods. Metal ions such as aluminum, titanium, vanadium, zirconium, gallium, copper, manganese, zinc, nickel, iron, cobalt, germanium, chromium and molybdenum may be added to the catalyst by impregnation, ion exchange, or by replacing a part of the lattice atoms as described in G. W. Skeels and E. M. Flanigen in M. Occelli, et al., eds., A.C.S. Symposium Series, Vol. 398, Buttersworth, pp. 420-435 (1989).

The composition of the invention is characterized by means of XRD, gas adsorption, $^{27}$Al-NMR and $NH_3$-IR (infrared). XRD and $^{27}$Al-NMR show that the zeolite structure remains unchanged after being incorporated into, or supported on, siliceous mesoporous material. However, $NH_3$-IR show the changes of hydroxyl groups after the incorporation of zeolite Beta. The extent of such changes of hydroxyl groups also depends on the zeolite loading in the final composite. While not wishing to be bound to any particular theory, it is believed that the interaction of zeolite with mesoporous matrix/support leads to a unique structure that is distinctly different from a simple, linear combination of the zeolite and mesoporous material. Moreover, the FTIR data shows that there is a frequency shift of the hydroxyl groups, consistent with an acidity modification.

In principle, the catalyst described herein can be used in all the processes in which zeolite-based catalyst is typically employed. For example, ZSM-11 can be used in virtually all of the reactions that are catalyzed by ZSM-5 (e.g., aromatics alkyation, xylene isomerization, dewaxing, etc.); ZSM-12 can be used in the processes of aromatics alkyation (e.g., production of p-diisopropylbenzene), aromatization, isomerization, dewaxing, etc.; ZSM-20 can be used in isomerization, alkene production, hydrocracking, and aromatization; ZSM-22 and ZSM-23 are useful for isomerization, alkene production, hydrocracking, and aromatization; ZSM-34 is useful for catalyzing methanol to olefins; ZSM-35 is useful for dewaxing, isomerization, aromatization, cracking and hydrogenation; ZSM-48 is useful for isomerization; PSH-3 and MCM-22 are active for aromatic alkylation, cracking, isomerization, aromatization, etc.; ITQ-1 can be used for cracking, oxidation, etc.; ITQ-2 is especially useful for cracking, hydration, alkylation, etc.; ITQ-21 is a very good catalyst for cracking; SAPO-5 is used in isomerization, dehydration, cracking; SAPO-34 is useful for dehydrogenation; SAPO-11 is useful for dewaxing and aromatics isomerization.

For example, catalytic cracking of petroleum feedstock (e.g. gas oil and vacuum gas oil) using a catalyst described herein can be carried out in FCC or TCC units at a temperature of from about 400° C. to about 650° C., a catalyst to feed weight ratio from about 3:1 to 10:1. Feeds for catalytic cracking can include petroleum fractions having an initial boiling point (IBP) of from about 200° C. to about 260° C. and an end boiling point (EBP) of from about 400° C. to about 455° C. Optionally, the feed can include petroleum fractions having components with boiling points above 540° C., such as deasphalted and undeasphalted petroleum residue, tar sand oil, shale oil, bitumen, or coal oil.

Alkylation of organic compounds with olefins employing catalyst described herein can be performed at a temperature of from about 90° C. to about 250° C., a pressure of from about 0.5 bar to about 35 bars, and a space velocity of from about 1 WHSV to about 20 WHSV.

Hydrocracking of hydrocarbons employing the catalyst described herein can be performed under reaction conditions including a temperature of from about 200° C. to about 400° C., a pressure of from about 10 bars to about 70 bars, and a space velocity of from about 0.4 WHSV to about 50 WHSV.

Hydroisomerization of hydrocarbons employing the catalyst described herein can be performed under reaction conditions including a temperature of from about 150° C. to about 500° C., a pressure of from about 1 bar to about 240 bars, and a space velocity of from about 0.1 WHSV to about 20 WHSV.

Catalytic dewaxing of hydrocarbons employing the catalyst described herein can be performed under a wide range of reaction conditions, e.g., a temperature of from about 150° C. to about 500° C., a pressure of from about 6 bars to about 110 bars, and a space velocity of from about 0.1 WHSV to about 20 WHSV.

Acylation of organic compounds (e.g., aromatics, alkylaromatics) employing the catalyst described herein can be conducted under reaction conditions including a temperature of from about 20° C. to about 350° C., a pressure of from about 1 bar to about 110 bars, and a space velocity of from about 0.1 WHSV to about 20 WHSV. Acylating agents include, for example, carboxylic acid anhydrides and acyl halides.

Aromatization of light hydrocarbon to aromatics using the catalyst described herein is preferably carried out under reaction conditions including a temperature of from about 600° C. to about 800° C., a pressure less than about 14 bars, and a space velocity of from about 0.1 WHSV to about 10 WHSV.

In some particular applications, the composition of the invention will show even more advantages than the conventional catalysts. For example, catalytic cracking of heavy feeds ideally needs some mild acidity on the mesoporous matrix/support, which can achieve pre-cracking of the very large molecules into moderate-sized molecules, and consequently the moderate-sized molecules further crack into the desired products. The composition of the invention may contain metals (e.g., aluminum) in the framework of the mesoporous matrix/support, offering mild acidity. Moreover, the high pore volume and high surface area provided by the mesoporous matrix/support can improve the tolerance to metals (e.g., V, Ni, Fe) and to sulfur, nitrogen, and oxygen species. Furthermore, the composition of the invention can be easily tuned by varying the type of zeolites employed, the amount of zeolite loading, and the mesoporosity, to meet some particular requirements for the processes.

The composition of the invention containing some metals (e.g., Ni, W, Pt, Pd, and combinations thereof) having (de)hydrogenation functions can be used as a catalyst for hydrocracking. The balance between the cracking activity and hydrogenation activity can be easily achieved by appropriate selection of the zeolite loading, the amount of metals in mesoporous matrix/support offering acidity, and the amount of metals with hydrogenation function. Normally, zeolite material has high cracking activity, and mesoporous materials have lower cracking activity. As such, the combination of zeolite and mesoporous matrix can be adjusted to provide the desired cracking activity. Therefore, the yield and selectivity can be optimized. For example, a high selectivity for middle distillate or diesel fuel can be achieved. In the production of lube base oils, the composition of the invention allows a range of feedstocks to be broadened, because mesoporous matrix/support offers precracking activity; it also improves the tolerance to heavy metals and other poisoning species.

The method of making the catalyst composition and the application of the catalytic composition of the present invention are illustrated by the following examples, but are not limited to these examples. In these examples the composition amounts are given in parts by weight.

EXAMPLE 1

First, 1.5 parts calcined zeolite beta with an Si/Al molar ratio of 25 and an average particle size of 1 μm were suspended in 16.3 parts water and stirred for 30 minutes. Then 20.3 parts tetraethylorthosilicate (TEOS) were added to the suspension with stirring. After continuous stirring for another 30 minutes, 9.3 parts triethanolamine were added. After stirring again for another 30 minutes, 4.0 parts tetraethylammonium hydroxide aqueous solution (35% solution available from Aldrich) were added drop-wise to the mixture to increase the pH. After stirring for about 2 hours, the mixture formed a thick non-flowing gel. This gel was aged at room temperature under static conditions for 17 hours. Next, the gel was dried in air at 100° C. for 28 hours. The dried gel was transferred into an autoclave and hydrothermally treated at 170° C. for 17.5 hours. Finally, it was calcined at 600° C. for 10 hours in air with a ramp rate of 1° C./min.

The final product was designated as Sample 1. The theoretical amount of zeolite beta present in the Sample 1 was 20 wt %. Sample 1 was characterized by XRD, TEM nitrogen porosimetry, argon porosimetry and NH$_3$-temperature programmed desorption (TPD). Pure zeolite beta was also characterized by XRD for purposes of comparison.

Referring to FIG. 1, the XRD pattern of the pure zeolite beta, depicted in plot 1-b, shows the most pronounced characteristic reflections at about 7.70 and 22.2° in 2 theta (θ) with a 33 minute scanning time. The XRD pattern of the mesoporous inorganic oxide support with the zeolite beta crystals (Sample 1) is depicted in plot 1-a. An intense peak at low angle is observed, indicating that Sample 1 is a meso-structured material. The peaks for zeolite beta are relatively small because the maximum theoretical zeolite content of the final product is only about 20 wt %. When the scanning time for Sample 1 was extended to 45 hours, the characteristic peaks of zeolite beta become clearly visible, as depicted in plot 1-c.

Figure 2:
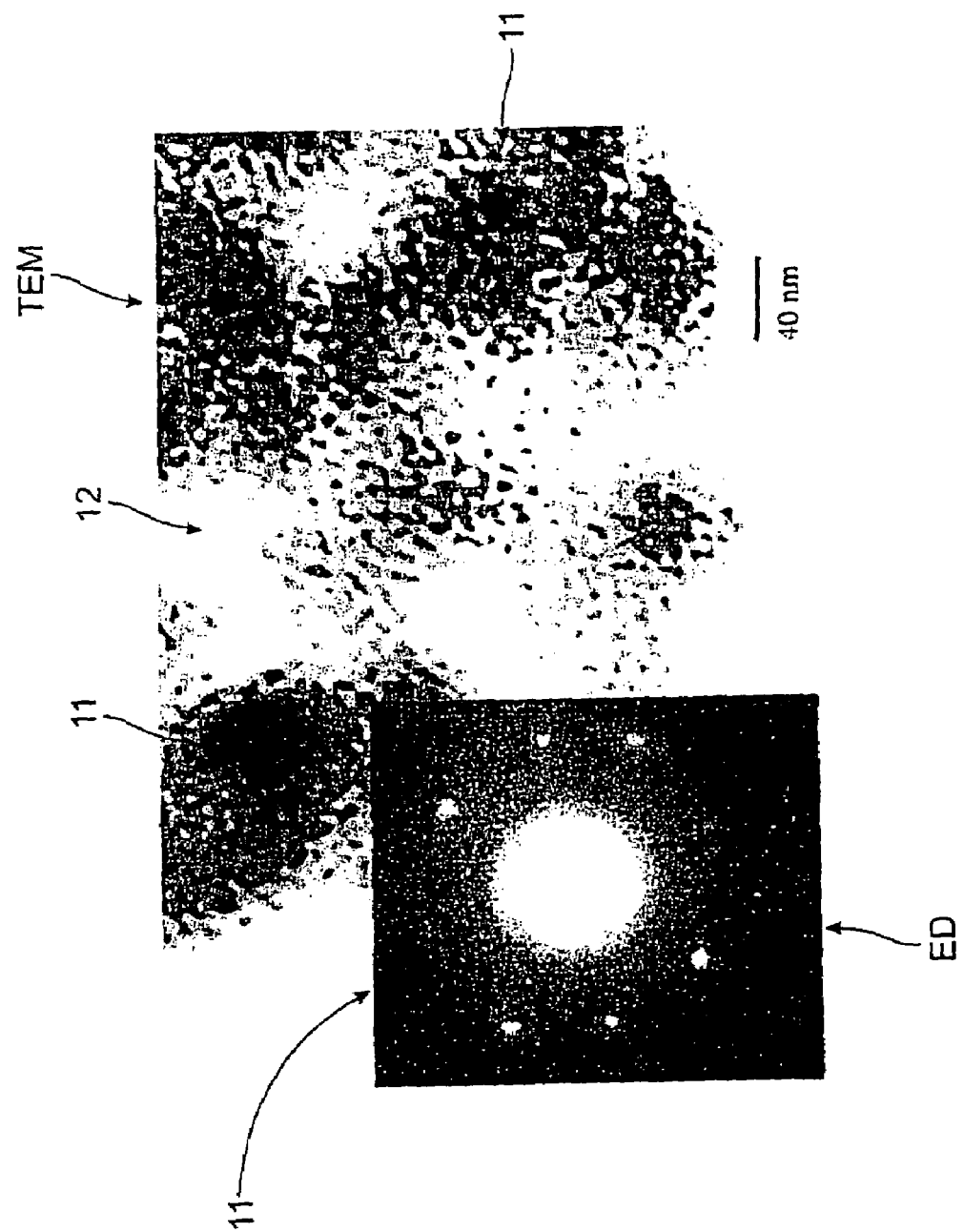
FIG. 2 is a high resolution transmission electron microscopy (TEM) image of the mesoporous inorganic oxide support with zeolite beta (Sample 1), and an inset showing an electron diffraction pattern of the zeolite domains.

Referring now to FIG. 2, a high-resolution TEM image of Sample 1 is depicted, which shows dark gray domains 11 in a mesoporous matrix 12. The inset "ED" depicts an electron diffraction pattern that confirms that the dark gray domains 11 are zeolite beta crystals.

Nitrogen adsorption shows that Sample 1 has a narrow mesopore size distribution, mainly centered at about 9.0 nm, high surface area of 710 m$^2$/g and high total pore volume of 1.01 cm$^3$/g. Argon adsorption shows a peak of micropore size distribution around about 0.64 nm, corresponding to micropore size in zeolite beta. The micropore volume of pores with a diameter smaller than 0.7 nm was 0.04 cm$^3$. This is about 16% of the micropore volume of the pure zeolite beta. Initial addition of uncalcined zeolite beta was 20 wt % based on the final composite. The zeolite beta weight decreased by about 20 wt % due to the template removal during calcination. Taking the mass loss of zeolite during calcination into account, the expected content of zeolite beta in the final composite is about 16 wt %, which is consistent with the value obtained from micropore volume.

Figure 3:
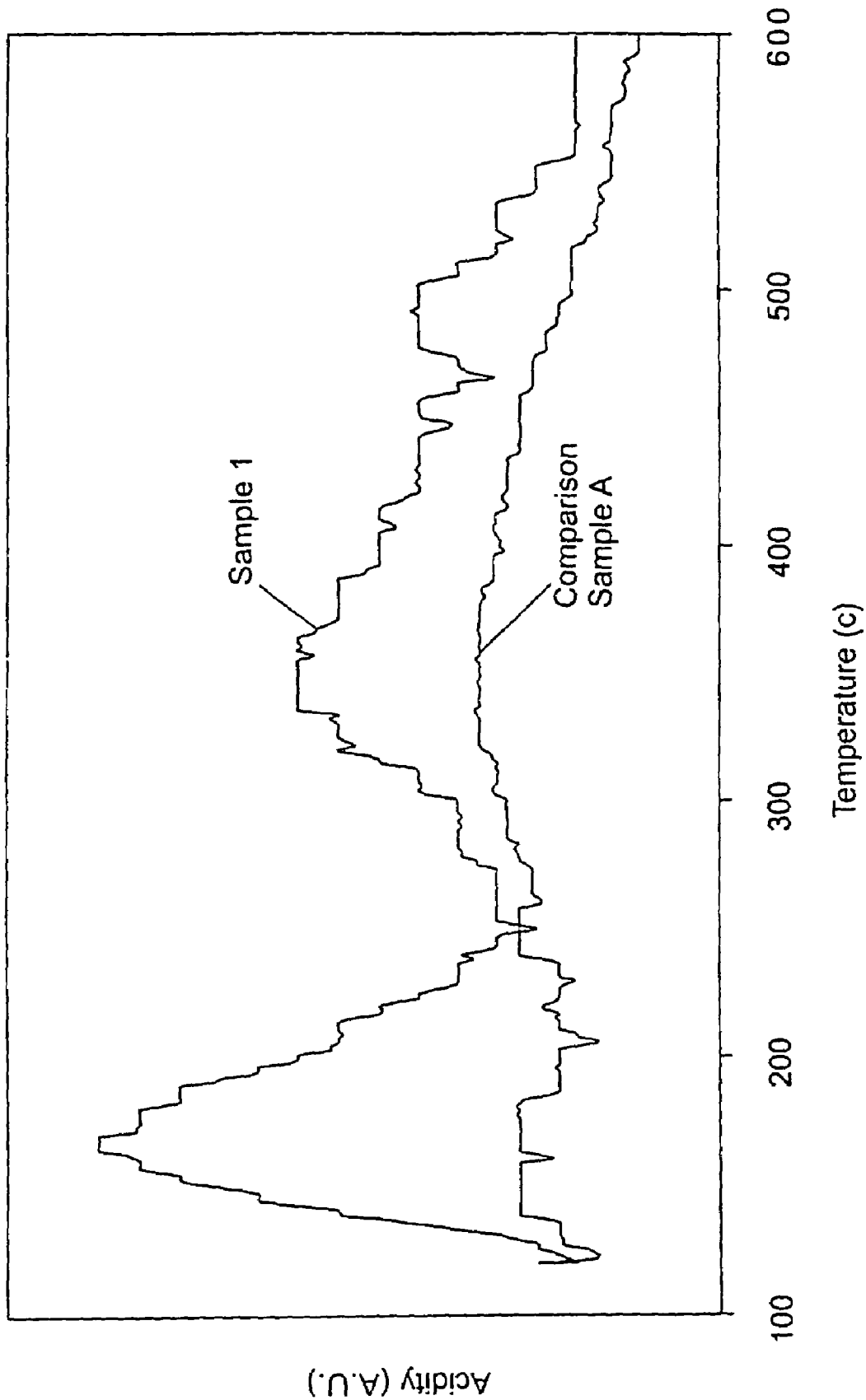
FIG. 3 is a chart showing the temperature programmed desorption of $NH_3$ ($NH_3$-TPD) analysis of the mesoporous inorganic oxide support with zeolite beta (Sample 1), and a comparison sample containing no zeolite beta.

Referring to FIG. 3, the NH$_3$-TPD measurement of Sample 1 showed two desorption peaks, indicating that there are strong acid sites similar to those in zeolites.

EXAMPLE 2

Figure 5:
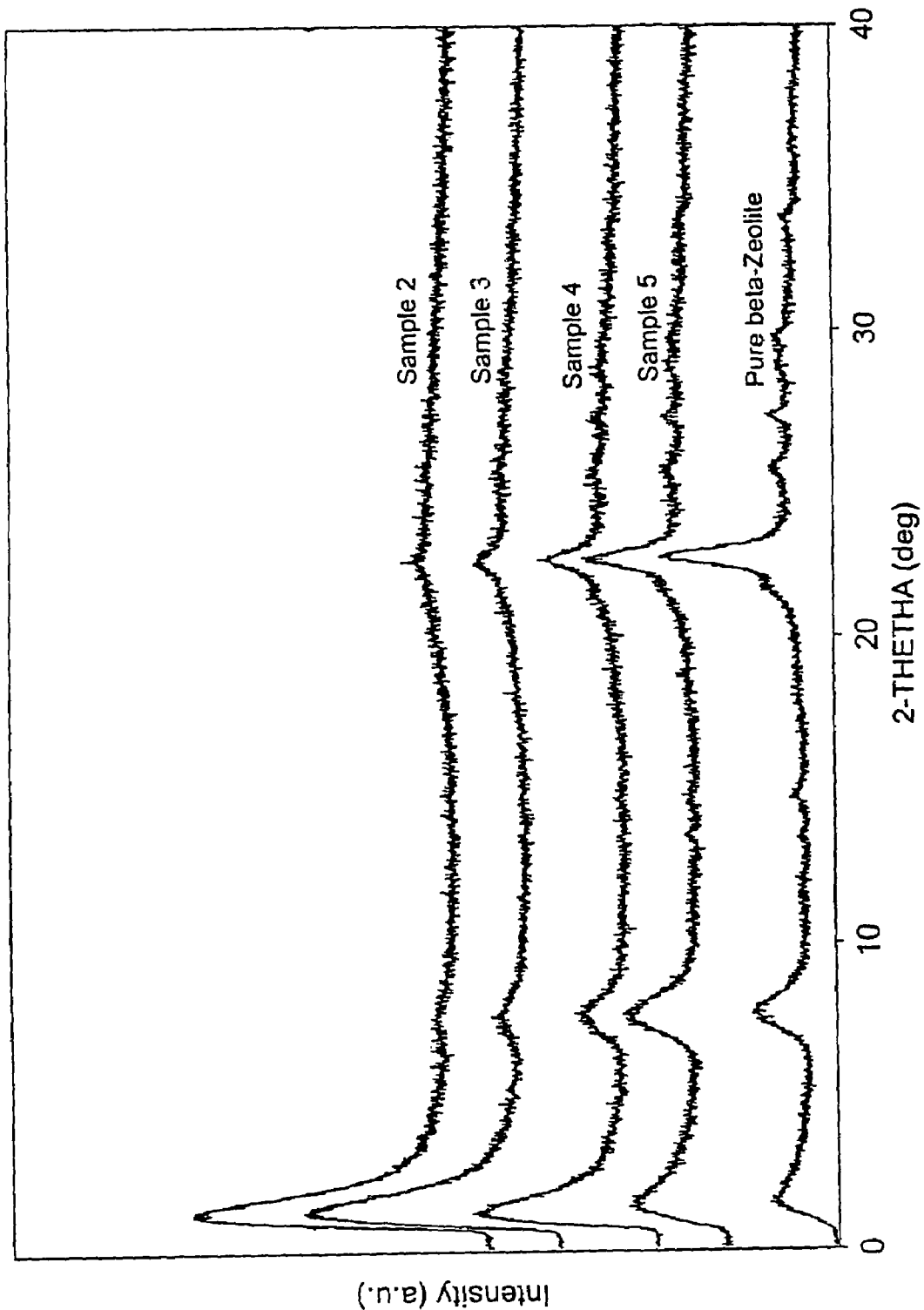
FIG. 5 is a chart showing the XRD patterns of the materials produced in Examples 2 to 5 herein, as well as pure zeolite beta.

First, 3.4 parts calcined zeolite beta with an Si/Al ratio of 150 and an average particle size of 0.2 μm were suspended in 85.0 parts water and stirred for 30 minutes. Then 105.8 parts TEOS were added to the suspension with stirring. After continuous stirring for another 30 minutes, 38.3 parts triethanolamine were added. After stirring again for another 30 minutes, 20.9 parts tetraethylammonium hydroxide aqueous solution (35%) were added drop-wise to the mixture. After stirring for about 2 hours the mixture turned into a thick non-flowing gel. This gel was aged at room temperature under static conditions for 24 hours. Next, the gel was dried in air at 98-100° C. for 24 hours. The dried gel was transferred into autoclaves and hydrothermally treated at 180° C. for 4 hours. Finally, it was calcined at 600° C. for 10 hours in air with a ramp rate of 1° C./min. The XRD pattern of the resultant product, designated as Sample 2, is shown in FIG. 5. There was about 10 wt % zeolite beta in the final composite.

EXAMPLE 3

Figure 4:
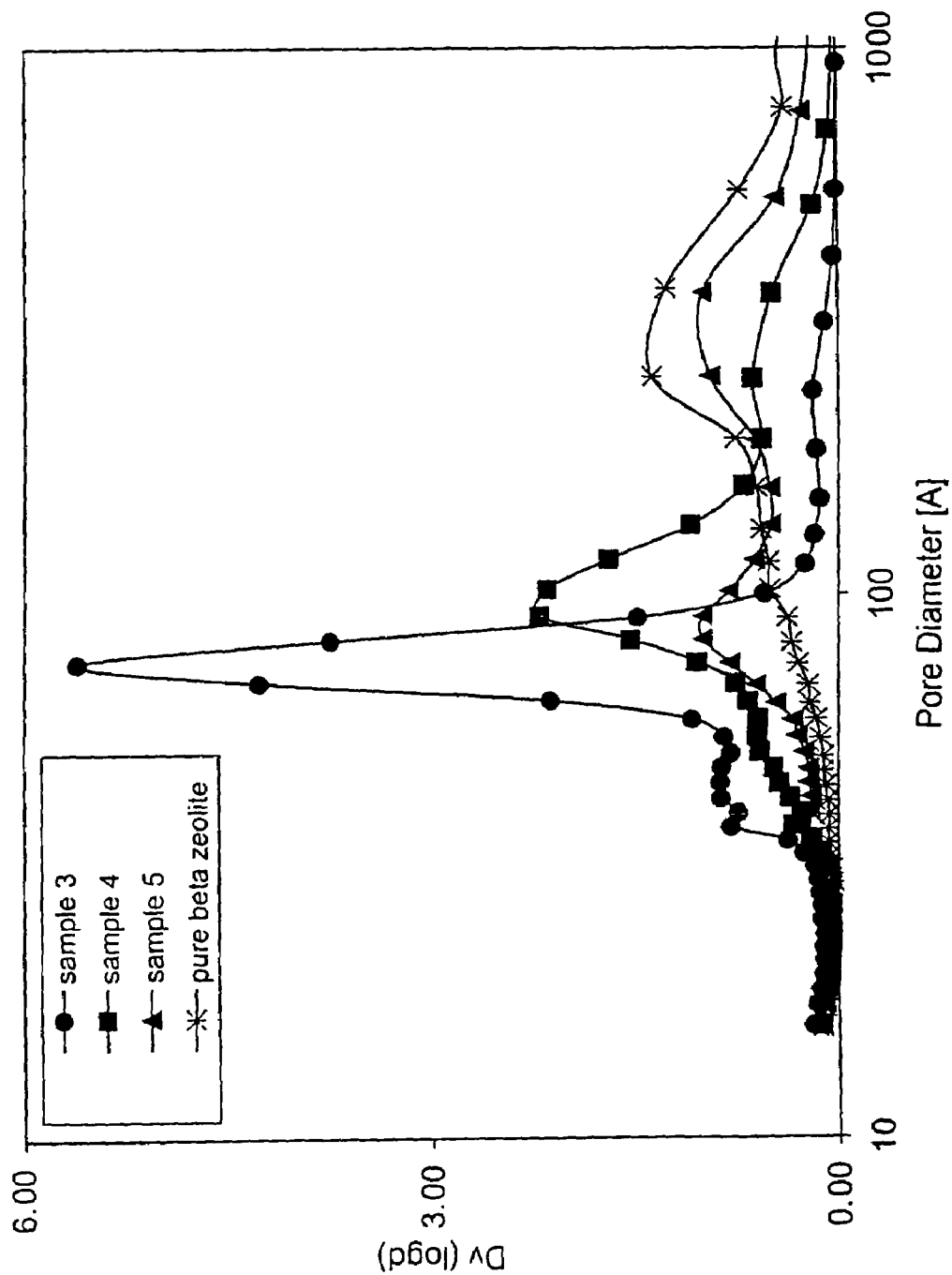
FIG. 4 is a graph showing the mesopore size distribution of the material produced in Examples 3, 4, and 5 herein, and of pure zeolite beta.

First, 4.6 parts calcined zeolite beta with an Si/Al ratio of 150 and an average particle size of 0.2 μm were suspended in 51.02 parts water and stirred for 30 minutes. Then 23.0 parts triethanolamine were added to the suspension with stirring. After continuous stirring for another 30 minutes, 63.5 parts TEOS were added. After stirring again for another 30 minutes, 12.6 parts tetraethylammonium hydroxide aqueous solution (35%) were added drop-wise to the mixture. After stirring for about 2 hours, the mixture formed a thick, non-flowing gel. This gel was aged at room temperature under static conditions for 24 hours. Next, the gel was dried in air at 100° C. for 24 hours. The dried gel was transferred into autoclaves and hydrothermally treated at 180° C. for 4 hours. Finally, it was calcined at 600° C. for 10 hours in air with a ramp rate of 1° C./min. The XRD pattern of the resultant product, designated as Sample 3, is shown in FIG. 5, which clearly shows two characteristic peaks of zeolite beta. There is about 20 wt % zeolite beta in the final composite. Nitrogen adsorption revealed its surface area of about 730 $m^2/g$, pore volume of about 1.08 $cm^3/g$. The mesopore size distribution of Sample 3 is shown in FIG. 4.

EXAMPLE 4

First, 12.2 parts calcined zeolite beta with an Si/Al ratio of 150 and an average particle size of 0.2 μm were suspended in 51.0 parts water and stirred for 30 minutes. Then 23.0 parts triethanolamine were added to the suspension with stirring. After continuous stirring for another 30 minutes, 63.5 parts TEOS were added. After stirring again for another 30 minutes, 12.7 parts tetraethylammonium hydroxide aqueous solution (35%) were added drop-wise to the mixture. After stirring for about 2 hours, the mixture formed a thick non-flowing gel. This gel was aged at room temperature under static conditions for 24 hours. Next, the gel was dried in air at 100° C. for 24 hours. The dried gel was transferred into autoclaves and hydrothermally treated at 180° C. for 4 hours. Finally, it was calcined at 600° C. for 10 hours in air with a ramp rate of 1° C./min. The XRD pattern of the resultant product, designated at Sample 4, is shown in FIG. 5, which clearly shows two characteristic peaks of zeolite beta. There is about 40 wt % zeolite beta in the final composite. Nitrogen adsorption revealed its surface area of about 637 $m^2/g$, pore volume of about 1.07 $cm^3/g$. Its mesopore size distribution is shown in FIG. 4.

EXAMPLE 5

First, 9.2 parts calcined zeolite beta with an Si/Al ratio of 150 and an average particle size of 0.2 μm were suspended in 17.0 parts water and stirred for 30 minutes. Then 7.6 parts triethanolamine were added to the above suspension under stirring. After continuous stirring for another 30 minutes, 21.2 parts TEOS were added. After stirring again for another 30 minutes, 4.2 parts of tetraethylammonium hydroxide aqueous solution (35%) were added drop-wise to the mixture. After stirring for about 2 hours, the mixture formed a thick, non-flowing gel. This gel was aged at room temperature under static conditions for 24 hours. Next, the gel was dried in air at 100° C. for 24 hours. The dried gel was transferred into three 50 ml autoclaves and hydrothermally treated at 180° C. for 4 hours. Finally, it was calcined at 600° C. for 10 hours in air with a ramp rate of 1° C./min. The XRD pattern of the resultant product, designated as Sample 5, is shown in FIG. 5, which clearly shows two characteristic peaks of zeolite beta. There was about 60 wt % zeolite Beta in the final composite. Nitrogen adsorption revealed its surface area of about 639 $m^2/g$, pore volume of about 0.97 $cm^3/g$. Its mesopore size distribution is shown in FIG. 4.

EXAMPLE 6

Eight parts of Sample 1 were mixed with two parts of alumina in the form of Nyacol to provide a catalyst. The mixture was dried and calcined by raising the temperature to 120° C. at the rate of 5° C./min, maintaining the 120° C. temperature for one hour, then raising the temperature at the rate of 5° C./min to 500° C. for five hours and finally lowering the temperature at the rate of 5° C./min to 150° C. and then allowing the catalyst to cool to room temperature in a desiccator. The catalyst was then manually crushed and sieved to −12/+20 mesh for activity testing. This catalyst contained 16 wt % zeolite beta in mesoporous support. A recirculating differential fixed-bed reactor was charged with 1.0 gram of catalyst. The recirculating rate (200 g/min) was about 33 times the feed rate (6.1 g/min). The loaded reactor was initially filled with benzene, the feed (benzene containing 0.35 wt % ethylene) was metered in with a metering pump when the reactor reached 190° C. The run was carried out for seven hours. The reaction conditions included a temperature of 190° C. a pressure of 350 psig and a space velocity of 6 WHSV. Feed samples were taken at the beginning, the middle and the end of the run. Product samples were taken every third minute and analyzed by gas chromatography. Based on a first-order rate equation, a rate constant of 0.30 $cm^3$/g-sec was obtained for the benzene alkylation with ethylene to form ethylbenzene for 16 wt % zeolite beta-containing catalyst. Alternatively, this value is equivalent of a value of 1.50 $cm^3$/g-sec for an 80 wt % of zeolite beta-catalyst.

COMPARISON EXAMPLE A

A wholly siliceous mesoporous support was made in accordance with the method described in Example 1 except that no zeolite was incorporated. The resulting support was designated as Comparison Sample A. An $NH_3$-TPD measurement was made of Comparison Sample A, and the resulting measurement is depicted in FIG. 3.

COMPARISON EXAMPLE B

A sample of zeolite beta obtained from a commercial supplier and containing 80 wt % zeolite beta (Si/Al ratio of 4.9) and 20% binder was resized to −12/+20 mesh. The pore size distribution of zeolite beta is depicted in FIG. 4. The activity of the pure zeolite beta of this Comparison Example was tested in the same alkylation reaction using the same methodology and apparatus described in Example 6 above. A first-order rate constant of 0.29 $cm^3$/g-sec was obtained.

Comparing the results of Example 6 with Comparison Example B, the catalyst of Example 6, which is in accordance with the present invention, has about five times greater activity than an equivalent amount of zeolite beta alone for the alkylation of benzene with ethylene. These results indicate that the integrity of the zeolite crystals in the mesoporous catalyst support is maintained during the synthesis of Sample 1. The results also demonstrate that the microporous zeolite beta in the mesoporous support of Sample 1 was still accessible after the synthesis of the catalyst and that the mesopores of the support facilitate mass transfer in aromatic alkylation reactions.

EXAMPLE 7

This example illustrates incorporation of MCM-22. First, 2.4 parts as-synthesized zeolite MCM-22 with an Si/Al ratio of 12.8 and an average particle size of 2.5 μm were suspended in 10.5 parts water and stirred for 30 minutes. Then 9.2 parts triethanolamine were added to the above suspension under stirring. After continuous stirring for another 30 minutes, 12.7 parts TEOS were added. After stirring again for another 30 minutes, 2.52 parts tetraethylammonium hydroxide aqueous solution (35%) were added drop-wise to the mixture. After stirring for about 2 hours, the mixture formed a thick, non-flowing gel. This gel was aged at room temperature under static conditions for 24 hours. Next, the gel was dried in air at 98° C. for 24 hrs. The dried gel was transferred into autoclaves and hydrothermally treated at 180° C. for 4 hours. Finally, it was calcined at 600° C. for 10 hours in air with a heating ramp rate of 1° C./min.

Figure 6:
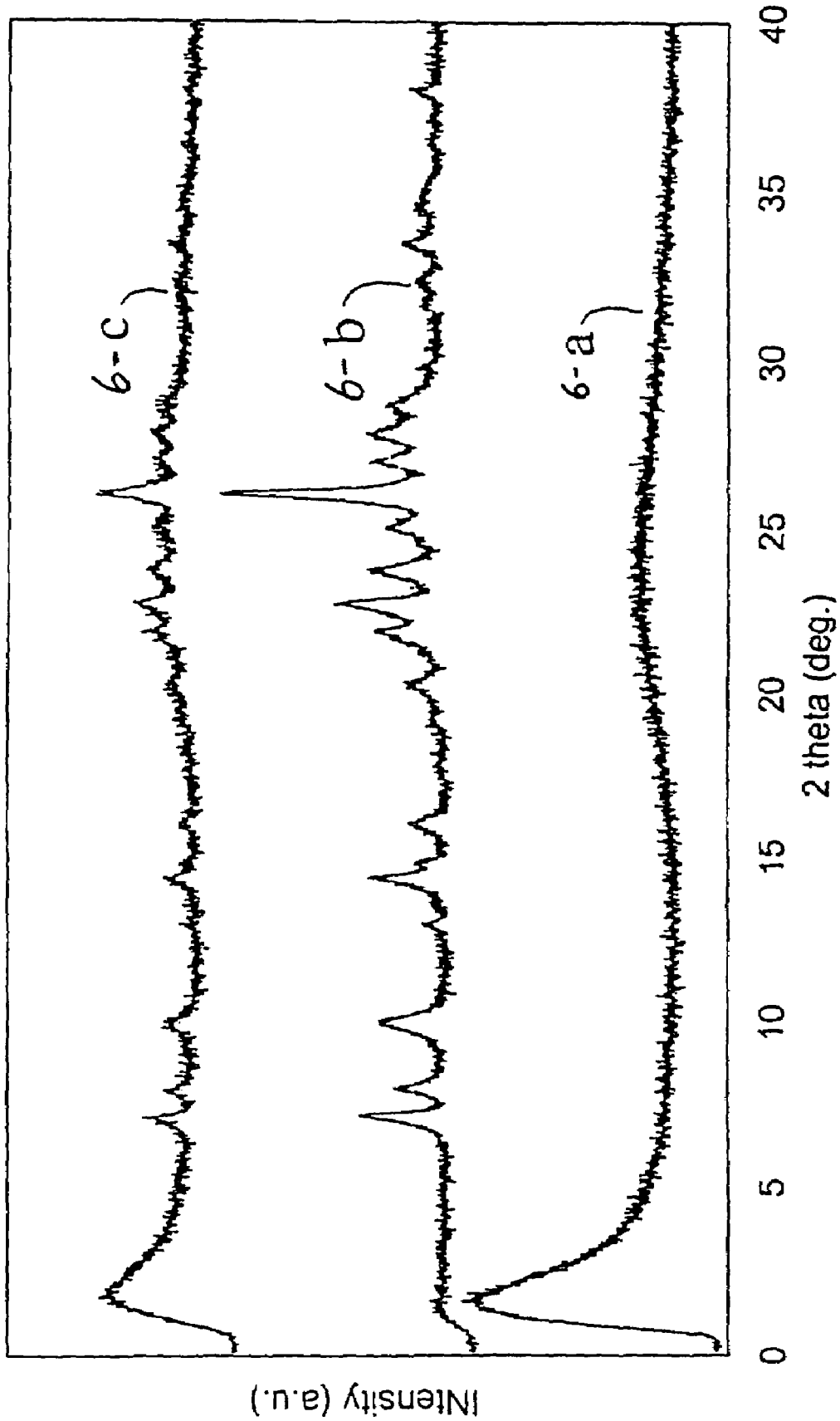
FIG. 6 shows the XRD patterns of the mesoporous material (plot 6-a), MCM-22 (plot 6-b), and the composite material of Example 7 (plot 6-c)

The XRD pattern of the resultant product, designated as Composite 7 and shown as plot 6-c in FIG. 6, clearly shows characteristic peaks of zeolite MCM-22 (plot 6-b) and mesoporous material (plot 6-a). There is about 40 wt % zeolite MCM-22 in Composite 7, and elemental analysis confirmed this number based on aluminum content, assuming no aluminum from siliceous mesoporous material. Nitrogen adsorption revealed its surface area of about 686 $m^2/g$, pore volume of about 0.82 $cm^3/g$. Its mesopore size distribution centered around 10 nm in FIG. 7. Argon adsorption showed micropores centered around 0.5 nm.

EXAMPLE 8

This example illustrates incorporation of MCM-56. First, 7.7 parts triethanolamine were mixed with 8.5 parts of distilled water for half an hour. Then, 2.0 parts of the $NH_4^+$-form zeolite MCM-56 (Si/Al molar ratio of 12.5) were added into the above solution under stirring. After continuous stirring for another 2 hours, 10.6 parts TEOS were added while stirring. After stirring again for another 30 minutes, 2.1 parts of tetraethylammonium hydroxide aqueous solution (35%) were added drop-wise to the mixture. The stirring continued until the mixture formed a thick, non-flowing gel. This gel was treated as same as that in Example 7 to get white powder.

Figure 7:
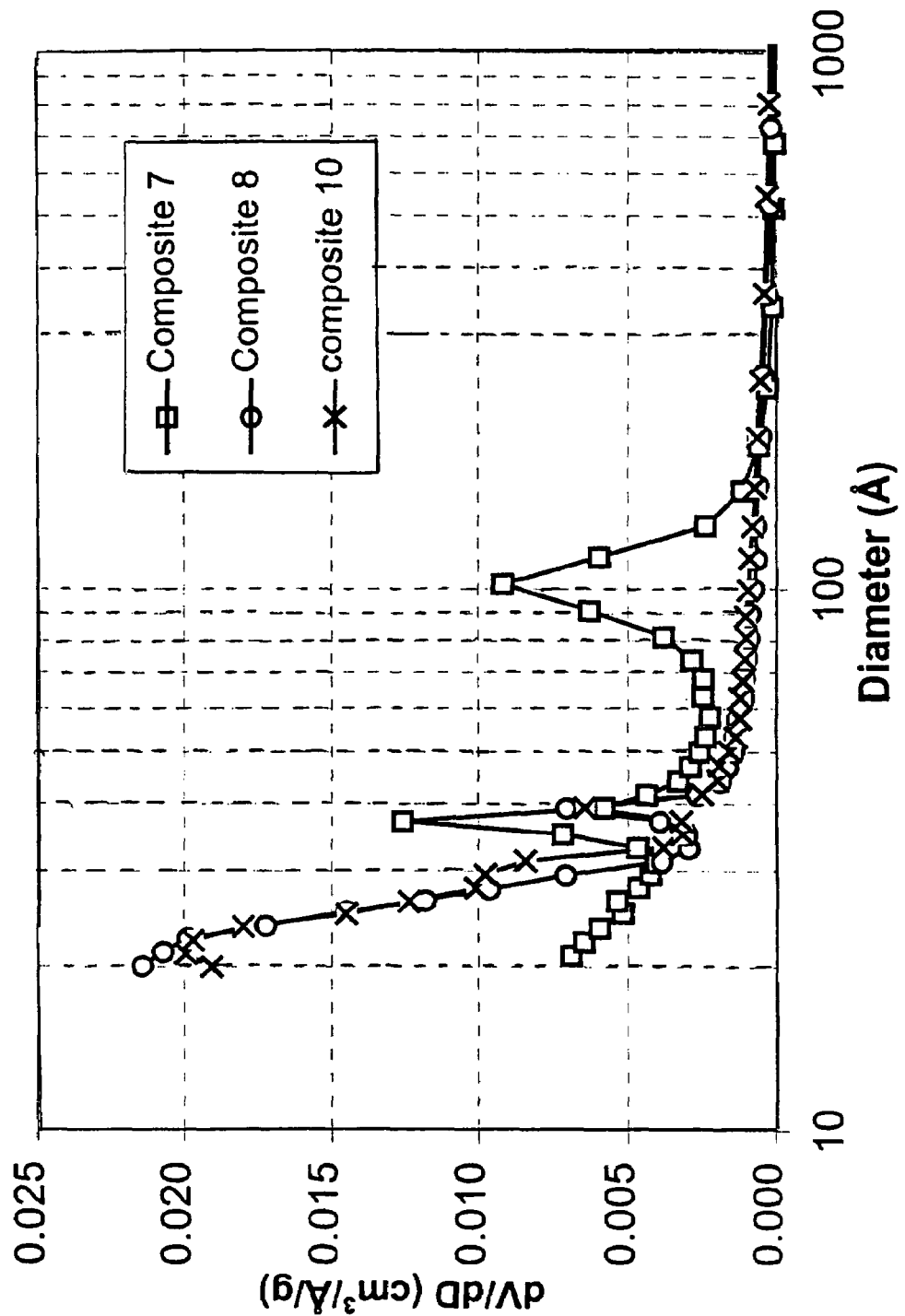
FIG. 7 shows the mesopore size distribution of the materials produced in Examples 7, 8 and 10.
Figure 8:
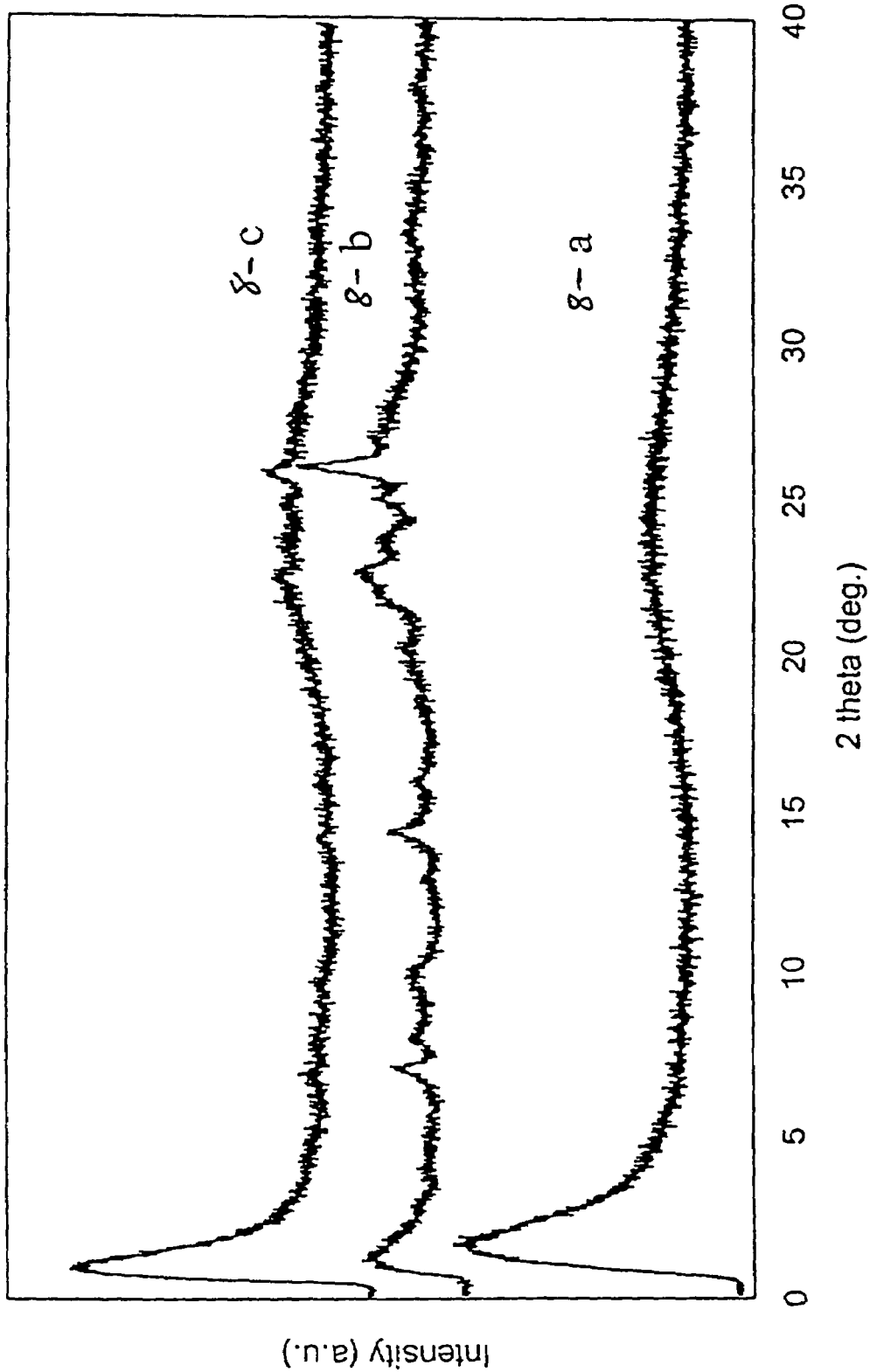
FIG. 8 shows the XRD patterns of the mesoporous material (plot 8-a), pure MCM-56 (plot 8-b), and Composite 8 (plot 8-c)

The XRD pattern of the resultant product, designated as Composite 8, shown as plot 8-c in FIG. 8, which clearly shows two characteristic peaks of zeolite MCM-56 and mesoporous material. Plot 8-b depicts the XRD pattern of zeolite MCM-56, and plot 8-a depicts the XRD pattern of mesoporous material. Elemental analysis showed that the total Si/Al ratio of the final composite was 43 and that the zeolite loading was about 33.3 wt % in the final composite. Nitrogen adsorption revealed its surface area of about 712 $m^2/g$ and a pore volume of about 0.96 $cm^3/g$. Its mesopore size distribution centered around 2.0 nm, shown in FIG. 7.

EXAMPLE 9

This example illustrates incorporation of ITQ-2. First, 15.2 parts of cetyltriethylammonium bromide (CTAB) was dissolved into 31.7 parts of water together with 32.7 parts of tetrapropylammonium hydroxide. Then 2.7 parts of as-synthesized MCM-22 was added into the above solution to get a suspension. The suspension was stirred in a flask placed in an 80° C. oil bath with reflux condenser for 18 hours to swell the lamellar structured zeolite MCM-22. The swollen MCM-22 was delaminated in an ultrasonic bath (135 w, 40 KHz) for an hour to get ITQ-2 zeolite. The ITQ-2 zeolite was washed and centrifuged until the pH value of the suspension dropped down to 8.

Figure 9:
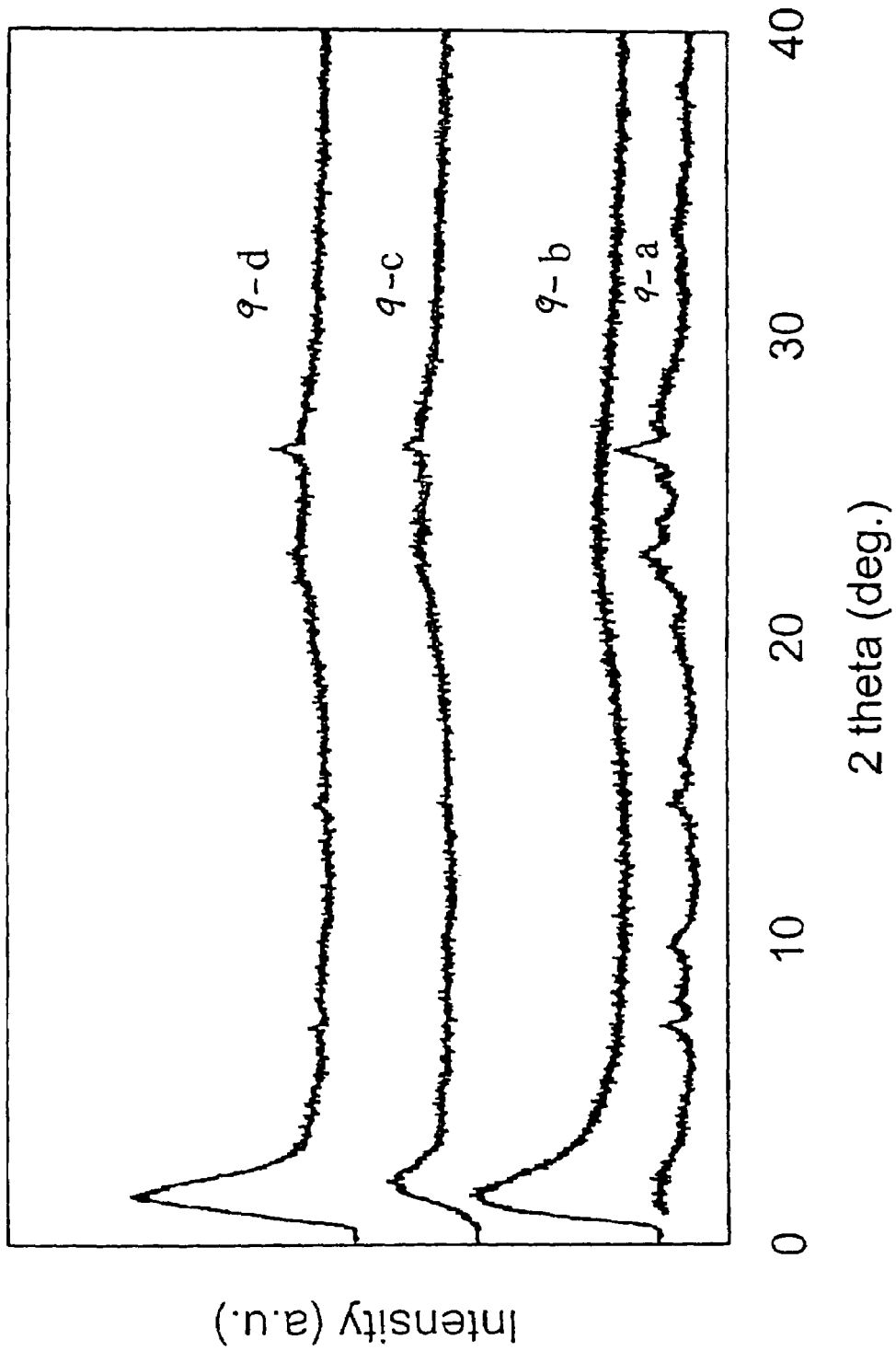
FIG. 9 shows the XRD patterns of pure ITQ-2 zeolite (plot 9-a), the mesoporous material (plot 9-b), the Composite 9 material (plot 9-c), and the Composite 10 material (plot 9-d)

ITQ-2 was re-suspended in 10 parts of water and then added into a mixture consisting of 9.2 parts of TEA and 12.7 parts of TEOS under stirring. After about 45 minutes a thick gel formed. The gel was treated the same as that in Example 7. The XRD pattern of the final composite, designated as Composite 9 and shown as plot 9-c in FIG. 9, clearly shows two characteristic peaks of zeolite ITQ-2 and mesoporous material. Plot 9-b depicts the XRD pattern of mesoporous material, and plot 9-a depicts the XRD pattern of zeolite ITQ-2. Elemental analysis showed that the total Si/Al ratio of the final composite was 36.9 and that the zeolite loading was about 32.3 wt % in the final composite. Nitrogen adsorption revealed a surface area of about 685 $m^2/g$, and a pore volume of about 0.40 $cm^3/g$. Its mesopore size distribution centered on 2.1 nm.

EXAMPLE 10

This example illustrates an "in-situ" incorporation of ITQ-2, in which MCM-22 transformation to ITO-2 was conducted in the course of mesopore formation. The chemicals and their amount of chemicals used were the same as in Example 9. First, as-synthesized MCM-22 was swollen in the same way as in Example 9. However, the swollen MCM-22 was not immediately delaminated. It was washed and subsequently centrifuged until no bromide was detected using silver nitrate solution. The swollen MCM-22 was re-suspended in water.

A bottle with a mixture consisting of TEA and TEOS was placed in an ultrasonic bath. The mixture was stirred by both sonication and a mechanical Teflon stirrer, meanwhile the swollen MCM-22 suspension was added. After about an hour of stirring, 2.5 parts of TEAOH (35%, tetraethyl ammonium hydroxide) was added and finally a thick gel formed. The gel was treated the same as that in Example 7. The XRD pattern of the final composite, designated as Composite 10 and shown as plot 9-d in FIG. 9, clearly shows two characteristic peaks of zeolite ITQ-2 (plot 9-a) and mesoporous material (plot 9-b). Elemental analysis showed that the total Si/Al ratio of Composite 10 was 32.4 and that the zeolite loading was about 50 wt % in the final composite. Nitrogen adsorption revealed its surface area of about 726 $m^2/g$, pore volume of about 0.78 $cm^3/g$. The mesopore size distribution was centered on 2.2 nm, as shown in FIG. 7.

EXAMPLE 11

Acylation of 2-methoxynaphthalene to 2-acetyl-6-methoxynaphthalene was performed in a stirred batch reactor. The reactor with 16.5 parts of catalyst, i.e., Composite 10 made in Example 10, was heated at 240° C. under vacuum for 2 hours and then filled with dry nitrogen. After the reactor was cooled down to 120° C., 250 parts of decalin (as a solvent), 31.6 parts 2-methoxynaphthalene, 40 parts of acetic anhydride and 10 parts of n-tetradecane (as an internal standard) was injected into the reactor. After reaction for six hours, the reactor mixture was analyzed by GC with WAX 52 CB column, and it was found that the conversion of 2-methoxynaphthalene reaches 56% with 100% selectivity to 2-acetyl-6-methoxynaphthalene.

EXAMPLE 12

Various catalysts made in the above examples were used to perform acylation of 2-methoxynaphthalene to 2-acetyl-6-methoxynaphthalene. The reaction conditions were the same as that in Example 11. In all tests the amount of zeolites in the reactor were kept the same as that in Example 11. In other words, the amount of catalyst (composite) was different due to different zeolite loading in the composites. Table 1 shows the comparison of reaction results over different catalysts.

TABLE 1

Comparison of acylation of 2-methoxynaphthalene on different catalysts

| Catalyst | Catalyst Description | Zeolite Loading % | Si/Al Ratio in Zeolite | Conversion (%) | Selectivity (%) |
|---|---|---|---|---|---|
| Composite 7 | MCM-22 Composite | 40.0 | 12.8 | 28.5 | 96 |
| Composite 8 | MCM-56 Composite | 33.3 | 12.5 | 53.4 | 96 |
| Composite 10 | ITQ-2 Composite | 50.0 | 12.8 | 56.2 | 96 |

EXAMPLE 13

Cracking of n-hexane was carried out in a fixed bed reactor. About 1 g of Sample 3, with a particle size of 125-250 µm obtained by crushing and sieving, was introduced into the reactor. For activation, the sample was heated in an air flow of 50 ml/min from room temperature to 600° C. with a heating rate of 10° C./min and held there for 8 hours. The cracking reaction of n-hexane was carried out under atmospheric pressure and with a n-hexane concentration of 6.6 mol % in nitrogen. The reaction temperature was varied from 500° C. to 570° C. in steps of 10° C. The modified contact time based on the mass of catalyst was kept constant at $1.4\ g_{cat}*min*l^{-1}$. For all measurements the n-hexane conversion was below 15% to avoid deactivation. It was found that the cracking of n-hexane could be described with apparent first order kinetics, and the first order reaction rate constants based on the zeolite mass were calculated for the different reaction temperatures. To compare the catalyst activities the reaction rate constant for 538° C. has been calculated with the Arrhenius equation that has been determined from four first order reaction rate constants. For Sample 3 the obtained reaction rate was $0.19\ g_{zeolite}^{-1}*min^{-1}*l$.

Figure 10:
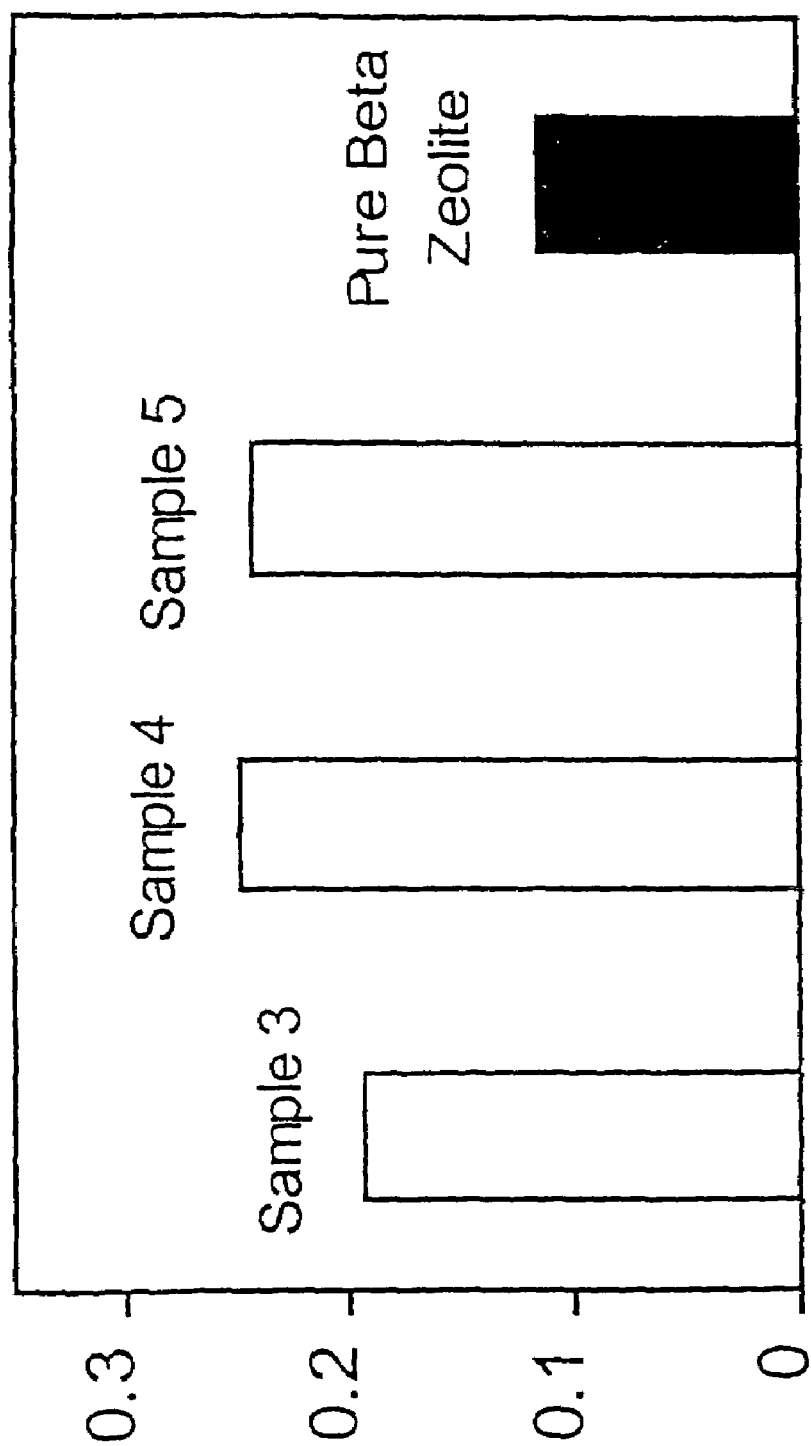
FIG. 10 shows the pseudo-first order reaction rate constant based on the mass of zeolite for n-hexane cracking at 538° C. with Samples 3, 4, 5 and pure beta zeolite.

A comparison was made with pure beta zeolite, and Samples 4 and 5 as follows:

A commercial zeolite beta with a Si/Al ratio of 150 was pressed into tablets and sieved to 125-250 µm. The activity of this pure zeolite beta, and those of Samples 4 and 5, were tested using the same methodology and apparatus described in Example 7 above. The reaction rate constants based on the mass of zeolite that characterize the activities of the catalysts are shown in FIG. 10. The activities of Sample 3, 4, and 5 are about two times higher than the activity of pure zeolite beta. The relative high activation energies of 150 kJ/mol, which have been measured, indicate that mass transfer did not influence the reaction of the relatively small n-hexane molecules.

EXAMPLE 14

FTIR spectra of the mesoporous support and pure zeolite Beta (Samples 3, 4, and 5) were recorded with a Bruker IFS88 spectrometer at a resolution of 4 cm$^{-1}$. All the samples were pelletized with KBr and placed in quartz cells permanently connected to a vacuum line (ultimate pressure $\leq 10^{-5}$ Torr) for thermal treatments under in situ conditions.

Figure 11:
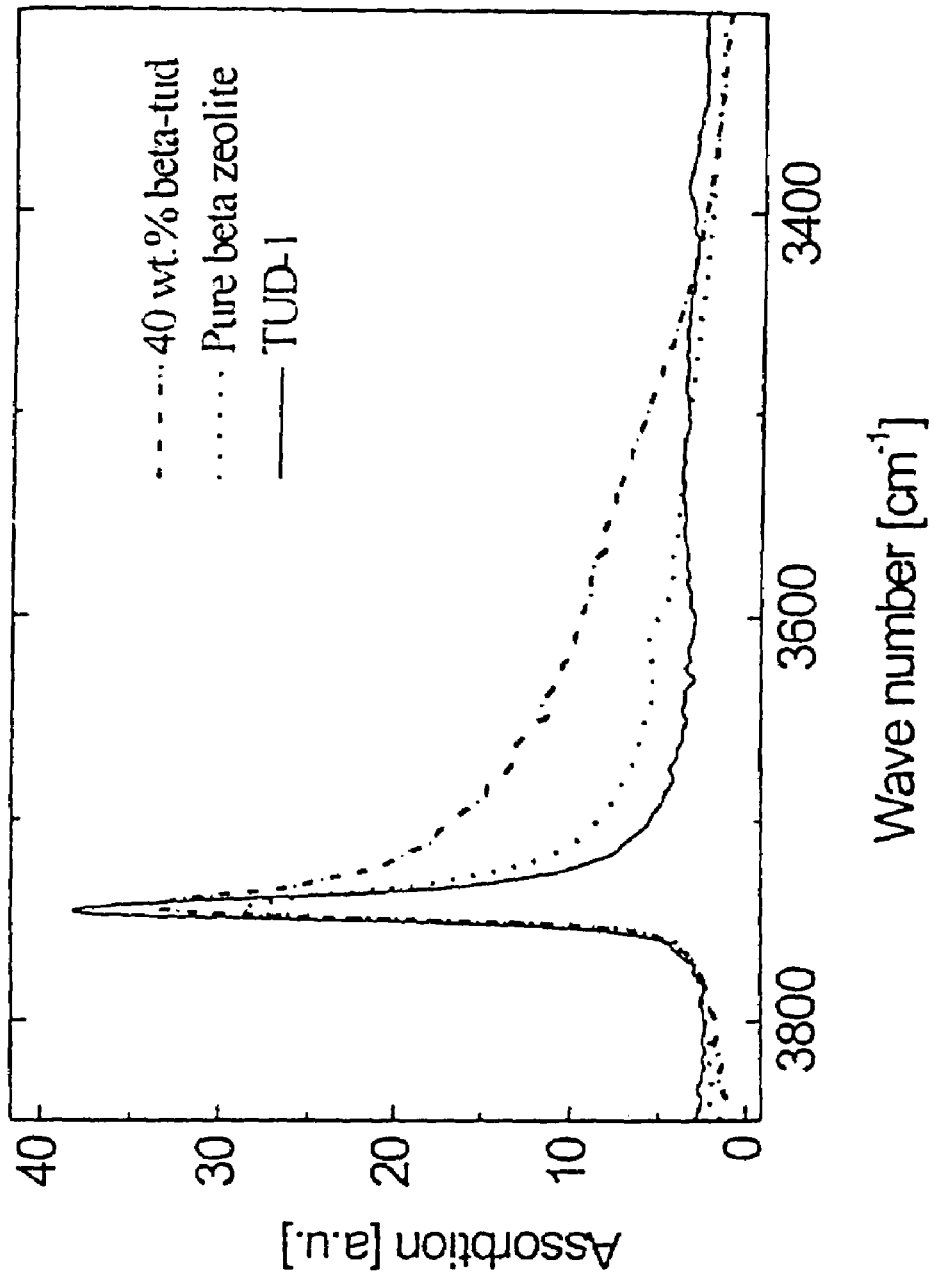
FIG. 11 shows the $NH_3$-IR spectra of the materials produced in Examples 4 and 5; and, FIG. 12 shows the XRD patterns of the materials produced in Examples 18 herein (plot 12-a), as well as pure USY zeolite (plot 12-b).

Referring to FIG. 11, the intensive peak at 3745 cm$^{-1}$ is conventionally assigned to silanol groups; a very small peak at 3610 cm$^{-1}$ (especially for zeolite Beta) can be assigned to its Bronsted acid sites, and the broad absorptions in the 3725-3650 cm$^{-1}$ region can be assigned to either H-bonded silanols or silanols close to Lewis acid centers. In general, the composition of the invention (Samples 3, 4, 5) showed a broad absorption in the 3725-3650 cm$^{-1}$ range compared to the zeolite Beta used and mesoporous support considered individually. It is interesting to note that the composite with 40 wt % zeolite Beta has the broadest distribution of hydroxyls in the 3725-3650 cm$^{-1}$ range. Moreover, the intensity of these hydroxyls is higher than in the other samples. FIG. 11 clearly shows that the composite with 40 wt % zeolite is distinctly different from either the mesoporous support or the pure zeolite Beta.

While not wishing to be bound to any particular theory, it is believed that the interaction between the nano-sized zeolite and the mesoporous matrix forms a unique, third structure that is different from a simple, linear combination of zeolite and mesoporous material. Moreover, there is a frequency shift of the hydroxyl group, consistent with an acidity modification. This can explain why 40 wt % zeolite loading has a pronounced change in acidity. This may be associated catalytic activity with respect to cracking of n-hexane in Example 13.

EXAMPLE 15

An ultrastable Y (USY) having a Si/Al molar ratio of 14.8 and a surface area of 606 m$^2$/g was incorporated into an aluminum-containing mesoporous matrix. First, 9.2 parts ultrastable zeolite Y were suspended in 17.0 parts water and stirred for 30 minutes. Then 7.7 parts triethanolamine were added to the above suspension under stirring. After continuous stirring for another 30 minutes, another mixture containing 21.2 parts of TEOS and 3.3 parts of aluminum isopropoxide were added under stirring. After stirring again for another 30 minutes, 4.2 parts tetraethylammonium hydroxide aqueous solution (35%) were added drop-wise to the mixture. After stirring for about 2 hours, the mixture formed a thick non-flowing gel. This gel was aged at room temperature under static conditions for 24 hours. Next, the gel was dried in air at 100° C. for 24 hours. The dried gel was transferred into an autoclave and hydrothermally treated at 180° C. for 2 hours. Finally, it was calcined at 600° C. for 10 hours in air with a ramp rate of 1° C./min. The final material was designated as composite 15.

Figure 12:
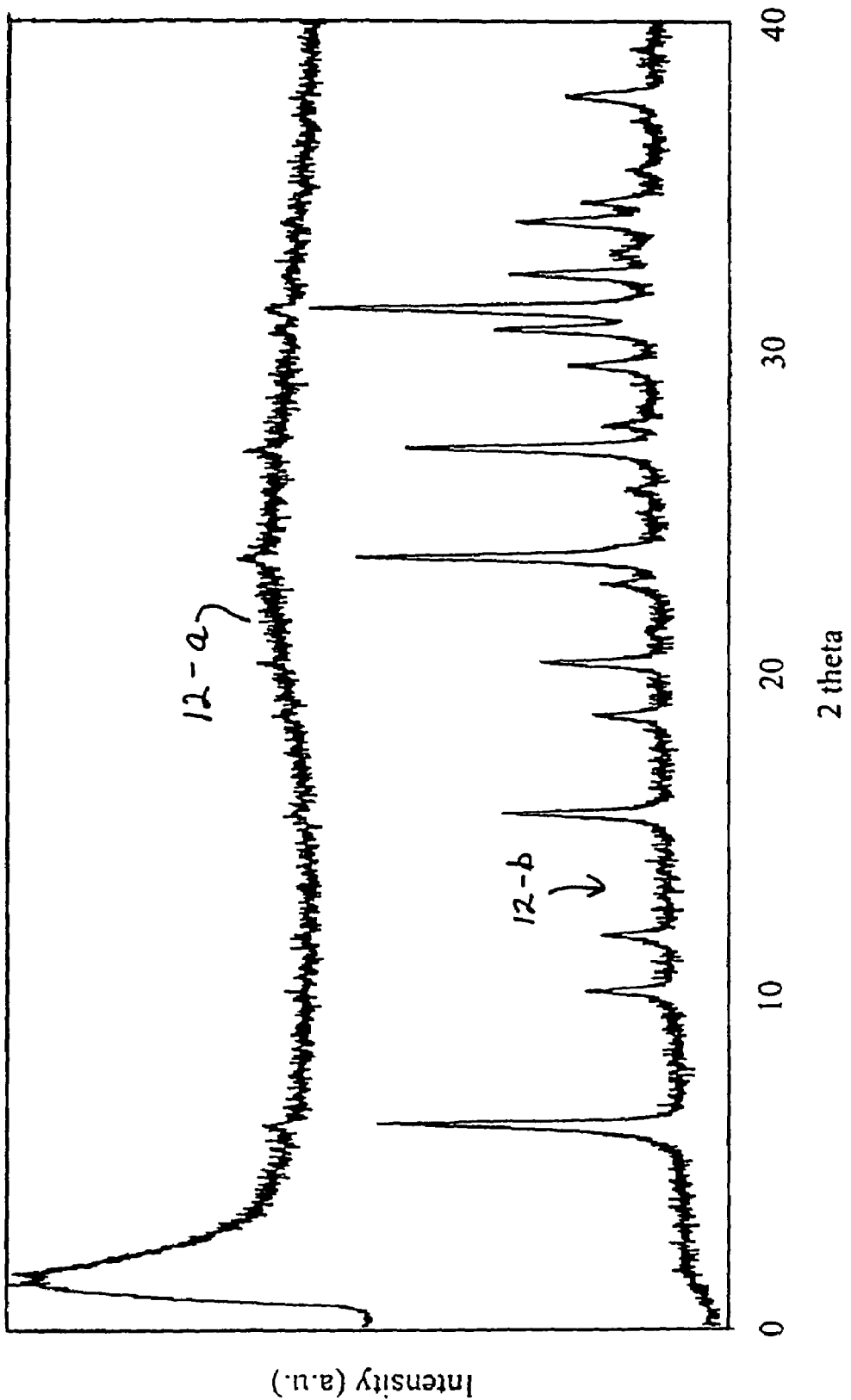

The XRD pattern of composite 15 is shown as plot 12-a in FIG. 12, which clearly shows two characteristic peaks of zeolite Y and mesostructure material. Plot 12-b depicts an XRD pattern of zeolite Y. There is about 60 wt % zeolite Y in the final composite. Nitrogen adsorption revealed its surface area of about 689 m$^2$/g, pore volume of about 0.99 cm$^3$/g.

EXAMPLE 16

A catalytic cracking catalyst is prepared using Composite 15. The proton form (H$^+$–) of the composite is obtained by ion-exchange, mixing one part of Composite 15 with ten parts of 1 N ammonium nitrate solution at 60° C. for 6 hours while stirring. The solid material is filtered, washed and dried at 110° C. to get a white powder. After a second ion-exchange, the solid material is calcined at 550° C. for 6 hours in air.

Eight parts of H$^+$–Composite 15 are mixed with two parts of alumina in the form of Nyacol to provide a catalyst. The mixture is dried and calcined by the following steps: (a) raising the temperature to 120° C. at the rate of 5° C./min, (b) maintaining the 120° C. temperature for one hour, (c) raising the temperature at the rate of 5° C./min to 500° C. for five hours, (d) lowering the temperature at the rate of 5° C./min to 150° C., and (e) then allowing the catalyst to cool to room temperature in a desiccator. The catalyst contains about 48% USY zeolite.

The catalyst was then steamed for 10 hours at 760° C. with 50% steam at atmospheric pressure. The final catalyst (containing USY, mesoporous matrix, and alumina binder) is designated as CAT16A.

For cracking activity comparison, a catalyst designated as CAT16B containing 48% of USY and binder alumina (without the mesoporous matrix) is prepared by ion-exchange, extrusion and steaming in the same way as in preparation of CAT16A.

Half each of these two catalysts are impregnated with vanadium naphthenate in toluene, resulting in 5000 ppm vanadium deactivation of FCC catalyst under commercial conditions. These two impregnated catalysts are designated as CAT16AV and CAT16BV, respectively.

EXAMPLE 17

The four catalysts prepared in Example 16 are evaluated for cracking activity using the fluidized activity test ("FAI") with fixed-fluidized bed FCC units at 400° C., catalyst/oil ratio of 2, 5 minutes on stream. The feed is Light East Texas Gas Oil (LETGO), and its properties are shown in Table 2. Comparison of Catalytic performance is shown in Table 3.

TABLE 2

Light East Texas Gas Oil (LETGO) properties

| | |
|---|---|
| API | 36.4 |
| Distillation (D1160): | |
| IBP, (vol %) | 235° C. |
| 10% | 254° C. |
| 30% | 268° C. |
| 50% | 287° C. |
| 70% | 307° C. |
| 90% | 341° C. |
| EBP | 364° C. |
| Bromine No. | 0.50 |
| KV @ 100° C., cSt | 1.30 |
| Avg. Molecular weight | 269 |
| Pour Point, ° C. | −7 |
| CCR, wt % | 0.02 |
| Refractive Index @ 70° | 1.4492 |
| Aniline Point, ° C. | 76 |
| Hydrogen, wt % | 13.3 |
| Sulfur, wt % | 0.13 |
| Total Nitrogen, ppm | 300 |
| Basic Nitrogen, ppm | 45 |
| Nickel, ppm | 0.1 |
| Vanadium, ppm | 0.1 |
| Iron, ppm | 0.77 |
| Copper, ppm | 0.05 |
| Paraffins, wt % | 44.7 |
| Naphthenes | 33.2 |
| Aromatics, wt % | 22.1 |

TABLE 3

Catalytic Performance

| Catalyst | Vanadium Content % | FAI % Conversion | Activity Retention % |
|---|---|---|---|
| CAT16A | 0 | 65.6 | |
| CAT16AV | 0.52 | 51.3 | 78.7 |
| CAT16B | 0 | 48.3 | |
| CAT16BV | 0.53 | 23.8 | 49.3 |

The results in Table 3 show that compositions of the invention improved the tolerance of heavy metals due to the acidic mesoporous matrix. Cracking activity is also improved by the novel combination of zeolite and acidic mesoporous matrix.

EXAMPLE 18

A composite, designated as Composite 18, containing USY zeolite was synthesized in the same way as described in Example 15. The only difference was the amount of chemicals used: 2.9 parts of USY zeolite, 28 parts of aluminum isopropoxide, 171.4 parts of tetraethyl orthosilicate, 34 parts of tetraethylammonium hydroxide, 124 parts of triethanolamine and 138 parts of water. The XRD pattern of Composite 18 is shown in FIG. 12, which clearly shows two characteristic peaks of zeolite Y and mesostructured material. The composite contained about 5 wt % USY zeolite, had a surface area of about 694 m$^2$/g, and a pore volume of about 1.1 cm$^3$/g.

The composite 18 was ion-exchanged into the proton form (H$^+$−) and extruded in the same way as described in Example 16. Finally, Composite 18 was formed into a cylindrical shape with a 1.6 mm diameter and contained about 4 wt % USY, 76 wt % of Al-containing mesoporous material and 20 wt % Al$_2$O$_3$.

Composite 18 was further functionalized by impregnation with Ni and W. Five (5) parts of nickel nitrate aqueous solution (14 wt % Ni) was mixed with 8.4 parts of ammonium metatungstate solution (39.8 wt % W) under stirring. The mixture was then diluted with 9 parts of water under stirring. 12.5 Parts of Composite 18 were impregnated with the above Ni/W solution, dried at 118° C. for 2 hours and calcined at 500° C. for 2 hours. The resulting modified Composite 18 was designated as CAT 18 and contained 4.0 wt % of Ni and 18.7 wt % W. It mainly featured a high amount of weakly acidic mesoporous matrix.

EXAMPLE 19

This Example illustrates the use of the material of Example 18 as a hydrocracking catalyst. Composite 18 prepared in Example 18 is evaluated for middle distillates selectivity in hydrocracking. The evaluation is carried out in a flow reactor with presulfided Composite 18 (in a conventional way) using a hydrotreated heavy vacuum gas oil as a feedstock. It is operated at LHSV of 1.5 kg/liter hour, total pressure of 140 bar (partial pressure of H$_2$S of 5.5 bar, and a partial pressure of ammonia of 0.075 bar) and a gas/feed ratio of 1500 NL/kg. The properties of feedstock are shown in Table 4.

TABLE 4

Hydrotreated Heavy Vacuum Gas Oil Properties
Distillation (D1160):

| | |
|---|---|
| IBP, ° C.(vol %) | 345 |
| 10% | 402 |
| 30% | 441 |
| 50% | 472 |
| 70% | 508 |
| 90% | 564 |
| EP | 741 |
| KV @ 100° C., cst | 8.81 |
| Carbon, wt % | 86.7 |
| Hydrogen, wt % | 13.4 |
| Total sulfur, wt % | 0.008 |
| Total Nitrogen, ppm | 16.1 |

The selectivity for middle distillates (e.g. boiling point range from 175° C. to 345° C.) is assessed at a net conversion of components of 65 wt %. Surprisingly, the selectivity reaches 72.6 wt %.

While the above description contains many specifics, these specifics should not be construed as limitations on the scope of the invention, but merely as exemplifications of preferred embodiments thereof. Those skilled in the art will envision many other possibilities within the scope and spirit of the invention as defined by the examples.

What is claimed is:

1. A composition comprising:
   a) at least one type of ordered, crystalline and microporous material with an average pore diameter less than 20 Angstroms;
   b) at least one type of non-crystalline inorganic oxide, said inorganic oxide having mesopores or mesopores and micropores and, wherein said inorganic oxide has a peak in an X-ray diffraction pattern between 0.5 and 2.5 degrees in 2θ, and wherein said mesopores are interconnected mesopores.

2. The composition of claim 1 wherein the said crystalline microporous materials are selected from a group consisting of zeolite Beta, zeolite Y, USY, mordenite, Zeolite L, ZSM-5, ZSM-11, ZSM-12, ZSM-20, Theta-1, ZSM-23, ZSM-34, ZSM-35, ZSM-48, SSZ-32, PSH-3, MCM-22, MCM-49, MCM-56, ITQ-1, ITQ-2, ITQ-4, ITQ-21, SAPO-5, SAPO-11, SAPO-37, Breck-6 and ALPO$_4$-5.

3. The composition of claim 1 wherein the at least one inorganic oxide has at least 97 volume percent mesopores based on micropores and mesopores of the inorganic oxide, a surface area of 400-1100 m$^2$/g, and a total pore volume of about 0.3-2.2 cm$^3$/g.

4. The composition of claim 3 wherein the mesopores have a size ranging from about 2 nm to about 25 nm.

5. The composition of claim 3 wherein the porous inorganic oxide is silicon oxide.

6. The composition of claim 1 further comprising at least one type of metal.

7. The composition of claim 6 wherein the metal is incorporated into the zeolite framework as substitutions of lattice atoms and/or located inside the zeolite micropores.

8. The composition of claim 6 wherein the metal is incorporated into the inorganic oxide inside at least one mesopore wall and/or on at least one mesopore surface.

9. The composition of claim 6 wherein the metal is at least one metal selected from the group consisting of aluminum, titanium, vanadium, zirconium, gallium, boron, manganese, zinc, copper, gold, lanthanum, chromium, molybdenum, nickel, cobalt, iron, tungsten, palladium and platinum.

10. The composition of claim 1 wherein the composition percentage by weight of the crystalline microporous material ranges from about 3% to about 90%.

11. The composition of claim 1 wherein the composition percentage by weight of the microporous zeolite ranges from about 4% to about 80%.

12. A method for making a catalytic material which comprises the steps of:
    a) pretreating a zeolite by one or more ion exchange, impregnation, immobilization of functional species and steaming;
    b) combining the pretreated zeolite with water, an inorganic oxide or a precursor of an inorganic oxide, and at least one mesopore-forming organic compound to form a mixture;
    c) drying the mixture;
    d) heating the dried mixture to a temperature and for a period of time sufficient to form a mesoporous inorganic oxide structure.

13. The method of claim 12 wherein the mesopore-forming organic compound is selected from the group consisting of glycerol, diethylene glycol, triethylene glycol, tetraethylene glycol, propylene glycol, triethanolamine, triisopropanolamine, starch, sulfolane, tetraethylene pentamine and diethylene glycol dibenzoate.

14. The method of claim 12 wherein said mesopore-forming organic compound has a boiling point of at least 150° C.

15. The method of claim 12 wherein the inorganic oxide is formed by reacting an inorganic oxide precursor with water.

16. The method of claim 12 wherein the mixture is maintained at a pH above about 7.0.

17. The method of claim 14 wherein the mixture is dried by heating in air at a temperature and for a period of time sufficient to drive off at least a major portion of the water and mesopore-forming organic compounds.

18. The method of claim 12 wherein the heating step (d) comprises heating the dried mixture to a temperature of from about 100° C. to about 250° C.

19. The method of claim 12 further comprising the step of calcining the heated dried mixture at a temperature of from about 300° C. to about 1000° C. for at least a period of time sufficient to effect removal of the mesopore-forming organic compound from the mesoporous, inorganic oxide support.

20. The method of claim 12 further comprising combining metal ions with the mixture, the metal being selected from the group consisting of aluminum, titanium, vanadium, zirconium, gallium, boron, manganese, zinc, copper, gold, lanthanum, chromium, molybdenum, nickel, cobalt, iron, tungsten, palladium and platinum.

21. The method of claim 12 further comprising the steps of admixing a binder with the catalytic material and forming the catalytic material into a predetermined shape.

22. The composition of claim 1 wherein the said crystalline microporous materials are selected from a group consisting of zeolite Y, USY, mordenite, Zeolite L, ZSM-5, ZSM-11, ZSM-12, ZSM-20, Theta-1, ZSM-23, ZSM-34, ZSM-35, ZSM-48, SSZ-32, PSH-3, MCM-22, MCM-49, MCM-56, ITQ-1, ITQ-2, ITQ-4, ITQ-21, SAPO-5, SAPO-11, SAPO-37, Breck-6 and ALPO$_4$-5.

23. The method of claim 12 wherein the mesoporous inorganic oxide structure has interconnected mesospores characterized by a peak in an X-ray diffraction pattern between 0.5 and 2.5 degrees in 2θ.

* * * * *